United States Patent
Schiell et al.

(10) Patent No.: US 6,962,943 B2
(45) Date of Patent: Nov. 8, 2005

(54) GABUSECTIN DERIVATIVES, PROCESSES FOR PREPARING THEM AND THEIR USE

(75) Inventors: Matthias Schiell, Brechen (DE); Martin Knauf, Root (CH); Luigi Toti, Hochheim (DE); Astrid Markus-Erb, Liederbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 206 days.

(21) Appl. No.: 10/290,607

(22) Filed: Nov. 8, 2002

(65) Prior Publication Data

US 2003/0187057 A1 Oct. 2, 2003

Related U.S. Application Data

(60) Provisional application No. 60/358,465, filed on Feb. 20, 2002.

(30) Foreign Application Priority Data

Nov. 21, 2002 (DE) .......................... 101 56 906

(51) Int. Cl.$^7$ ..................... A61K 31/40; C07D 207/04; A01P 31/00
(52) U.S. Cl. ...................................... 514/425; 548/544
(58) Field of Search ........................... 548/544; 514/425

(56) References Cited

U.S. PATENT DOCUMENTS 6,476,062 B2 * 11/2002 Chu et al. ................... 514/425
2002/0137788 A1    9/2002 Vertesy

FOREIGN PATENT DOCUMENTS

WO    WO 01/74772    10/2001
WO    WO 02/046152    6/2002

OTHER PUBLICATIONS

Royles, Brodyck J. L., Naturally Occuring Tetramic Acids: Structure, Isolation and Synthesis, Chemical Reviews, 1995, vol. 95, No. 6, pp. 1981–2001.

* cited by examiner

Primary Examiner—Rita Desai
Assistant Examiner—Robert Shiao
(74) Attorney, Agent, or Firm—Jiang Lin

(57) ABSTRACT

The present invention relates to compounds of the formula (I)

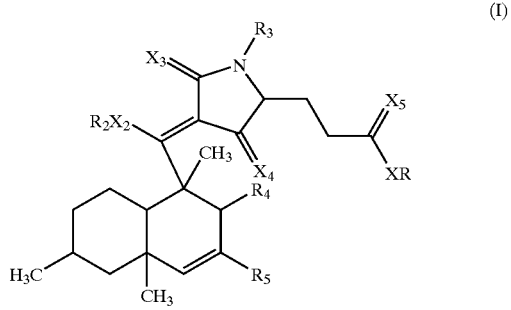

which are formed by the microorganism ST 003236 (DSM 14476) during fermentation, to a process for preparing and derivatizing them, to a pharmaceutical which comprises a compound of the formula (I) and to the use thereof for producing a pharmaceutical.

14 Claims, No Drawings

GABUSECTIN DERIVATIVES, PROCESSES FOR PREPARING THEM AND THEIR USE

A large number of antibiotics are used therapeutically for treating infectious diseases of bacterial origin. However, the pathogens are becoming increasingly resistant to the pharmaceuticals employed; Even what are termed multiresistant organisms, which have become resistant not only to individual antibiotic groups, such as β-lactam antibiotics, glycopeptides or macrolides, but also carry several resistances simultaneously, pose a great threat. There are even pathogens which have become resistant to all the commercially available antibiotics. Infectious diseases which are caused by these organisms can no longer be treated. There is therefore a great need for novel medicines which can be used against resistant organisms. While many thousand antibiotics have been described in the literature, most of them are too toxic to be able to be used as pharmaceuticals.

A relatively large number of antibiotics having a tetramic acid basic structure have already been described. Tetramic acid, i.e. 2,4-pyrrolidinedione, is the parent compound for a variety of natural products which are formed by some microorganisms and marine invertebrates.

harzianic acid, an antibiotic which possesses very little activity, was described in 1994 (R. Sawa et al., J. Antibiotics, 47, 731-732,1994);

The natural tetramic acid derivatives which were published up until 1994 are described in a review by B. J. L. Royles (Chem. Rev. 95, pages 1981-2001, 1995). Further natural tetramic acids, some of which possess antibacterial properties, have been described since 1995:

reutericyclin (A. Höltzel et al., Angew. Chem. 112, 2886-2888, 2000), a compound which possesses slight antibacterial activity;

equisetin and phomasetin (S. S. Singh et al., Tetrahedron Lett. 39, 2243-2246, 1998) are isomeric inhibitors of HIV-1 integrase;

cryptocin (J. Y. Li et al., Org. Lett. 2, 767-770, 2000), which is an antimycotic compound;

vancoresmycin (N. V. S. Ramakrishna et al., Int. Patent Publication No. WO 0028064), an antibiotic;

coniosetin (L. Vertesy et al., German patent application No. DE 10060810.8), a potent antibiotic composed of a tetramic acid moiety and a naphthyl moiety.

It has been found, surprisingly, that the strain ST 003236 (DSM 14476) is able to form the novel antibiotic gabusectin, which is not only very active against bacteria but is also well tolerated.

The invention accordingly relates to the compounds which are formed by the strain ST 003236 (DSM 14476) and to their physiologically tolerated salts, stereoisomers, tautomers, derivatives, in particular ester derivatives, and obvious chemical equivalents, such as ethers.

The invention relates to compounds of the formula (I)

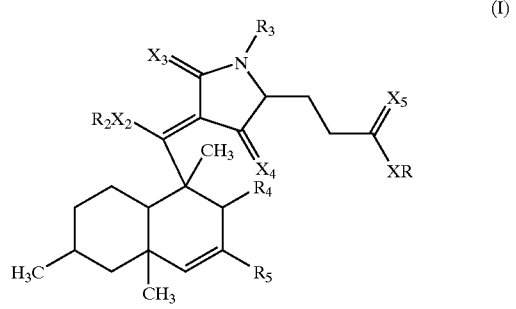

(I)

where
R, $R_2$ and $R_3$ are, independently of each other:
1. H, or
2. $C_1$–$C_6$-alkyl, $C_2$–$C_6$-alkenyl or $C_2$–$C_6$-alkynyl, in which alkyl, alkenyl and alkynyl are straight-chain or branched and are optionally substituted, once or twice, by:
   2.1 —OH,
   2.2 =O,
   2.3 —O—$C_1$–$C_6$-alkyl, in which alkyl is straight-chain or branched,
   2.4 —O—$C_2$–$C_6$-alkenyl, in which alkenyl is straight-chain or branched,
   2.5 -aryl,
   2.6 —NH—$C_1$–$C_6$-alkyl, in which alkyl is straight-chain or branched,
   2.7 —NH—$C_2$–$C_6$-alkenyl, in which alkenyl is straight-chain or branched,
   2.8 —$NH_2$ or
   2.9 halogen,
in which the substituents 2.3 to 2.7 can be further substituted by —CN, -amide or -oxime functions,
$R_4$ is $C_1$–$C_6$-alkyl or $C_2$–$C_6$-alkenyl, in which alkyl and alkenyl can be straight-chain or branched and are optionally substituted once or twice, as described under 2.1 to 2.9,
$R_5$ is H or methyl,
X, $X_2$, $X_3$, $X_4$ and $X_5$, are, independent of each other O, NH, N—$C_1$–$C_6$-alkyl, N—$C_2$–$C_6$-alkenyl, N—$C_2$–$C_6$-alkynyl, N-acyl, N-aryl, N—O—R or S,
or a stereoisomeric form or a tautomeric form of the compound of the formula (I) or a mixture of the previously mentioned forms in any ratio, or a physiologically tolerated salt of the compound of the formula (I) or of a stereoisomeric form or of a tautomeric form of a compound of the formula (I).

$C_1$–$C_6$-alkyl is a straight-chain or branched alkyl having from 1 to 6 C atoms, preferably having from 1 to 4 C atoms, e.g. methyl, ethyl, 1-propyl, tert-butyl and hexyl.

$C_2$–$C_6$-alkenyl is a straight-chain or branched alkenyl which has from 2 to 6 C atoms, and which is unsaturated once, twice or three times, e.g. allyl, crotyl, 1-propenyl, penta-1,3-dienyl and pentenyl.

$C_2$–$C_6$-alkynyl is a straight-chain or branched alkynyl which has from 2 to 6 C atoms, and which is saturated once or twice, e.g. propynyl, butynyl and pentynyl.

Aryl is phenyl, benzyl or 1- or 2-naphthyl, which can also be additionally substituted, for example by halogen, such as chlorine, bromine, fluorine, by alkyl having 1–4 C atoms, preferably methyl-, by hydroxyl, by alkoxy having 1–4 C atoms, in particular methoxyl, or by trifluoromethyl.

Acyl can be aliphatic or aromatic acyl radicals. Aliphatic acyl has 1–7, preferably 1–4, C atoms, such as formyl, acetyl, propionyl, butyryl, hexanoyl, acryloyl, crotonoyl, or propioloyl, which can be still further substituted, for example by halogen, such as chlorine, bromine or fluorine, by amino, or by alkylamino having 1–4 C atoms, preferably methyl or ethylamino groups. Aromatic acyl can, for example, be benzoyl or naphthoyl which can also be additionally substituted, for example by halogen, such as chlorine, bromine or fluorine, by alkyl having 1–4 C atoms, preferably methyl, by hydroxyl, by amino groups, such as ethylamino, or by alkoxy groups having 1–7, preferably 1–4, C atoms, in particular methoxy.

The invention preferably relates to a compound of the formula (I), where
R is 1.0 H, or
2.0 $C_1$–$C_6$-alkyl, $C_2$–$C_6$-alkenyl or $C_2$–$C_6$-alkynyl, in which alkyl, alkenyl and alkynyl are straight-chain or branched and are optionally substituted once or twice by:

2.1 —OH,
2.2 =O,
2.3 —O—$C_1$-$C_6$-alkyl, in which alkyl is straight-chain or branched,
2.4 —O—$C_2$-$C_6$-alkenyl, in which alkenyl is straight-chain or branched,
2.5 -aryl,
2.6 —NH—$C_1$-$C_6$-alkyl, in which alkyl is straight-chain or branched,
2.7 —NH—$C_2$-$C_6$-alkenyl, in which alkenyl is straight-chain or branched,
2.8 —$NH_2$ or
2.9 halogen,
in which the substituents 2.3 to 2.7 can be additionally substituted by —CN, -amide or -oxime functions,
$R_2$ is H,
$R_3$ is $CH_3$,
$R_4$ is $CH_3$,
$R_5$ is —CH=CH—$CH_3$, and
X, $X_2$, $X_3$, $X_4$ and $X_5$ are O.

Particularly preferably, the invention relates to a compound of the formula (I), where
R is H,
$R_2$ is H or $CH_3$,
$R_3$ is $CH_3$,
$R_4$ is $CH_3$,
$R_5$ is —CH=CH—$CH_3$, and
X, $X_2$, $X_3$, $X_4$ and $X_5$ are O.

Tautomeric forms of the compound of the compound (I) are, for example, a compound of the formula (II)

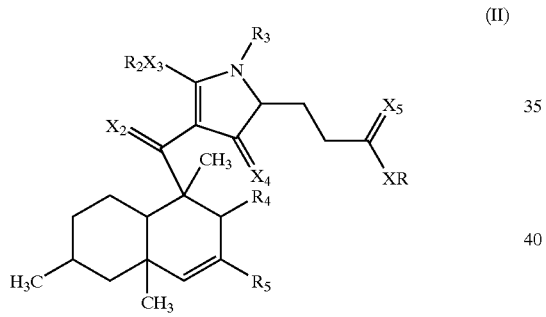

(II)

where the radicals R, $R_2$, $R_3$, $R_4$, $R_5$, X, $X_2$, $X_3$, $X_4$ and $X_5$ are defined as above, where tautomeric forms of the compounds of the formula (I) result, for example, from the hydrogen-bonded tetramic acid structural moiety,

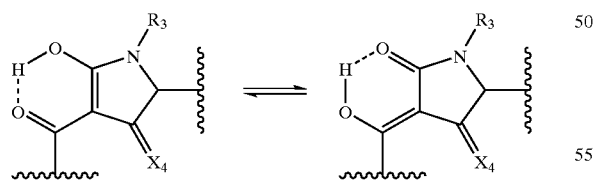

and are converted into each other in solution in dependence on parameters such as pH and solvent polarity.

Unless otherwise indicated, chiral centers in the compounds of the formula (I) and (II) can be present in the R configuration or in the S configuration. The invention relates both to the optically pure compounds and to stereoisomeric mixtures, such as enantiomeric mixtures and diasteromeric mixtures, in any ratio.

Of the compounds of the formula (I) and (II) according to the invention, preference is given to those compounds in which the configuration corresponds to the substituted hydrogenated naphthyl backbone of the formula (III):

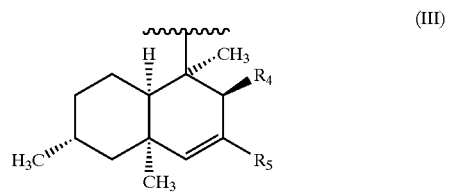

(III)

The invention furthermore relates to a compound of the formula (IV),

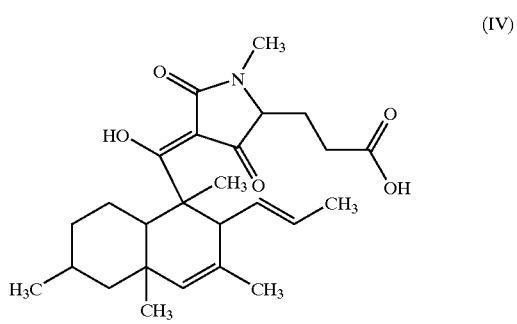

(IV)

to a compound of the formula (V),

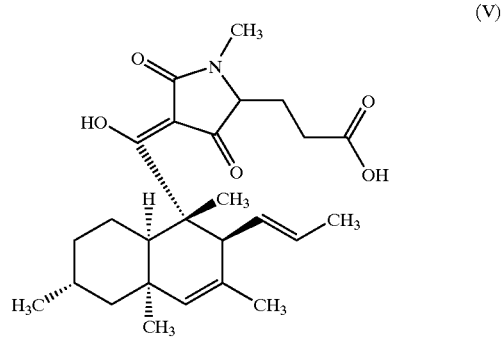

(V)

to a compound of the formula (VI),

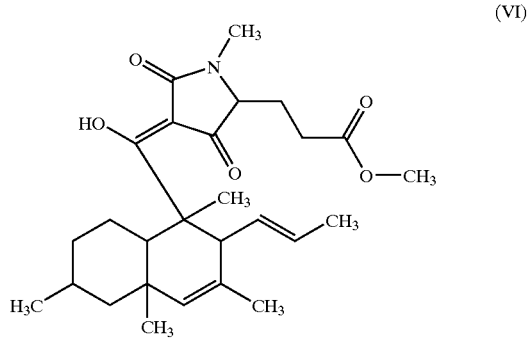

(VI)

to a compound of the formula (VII),

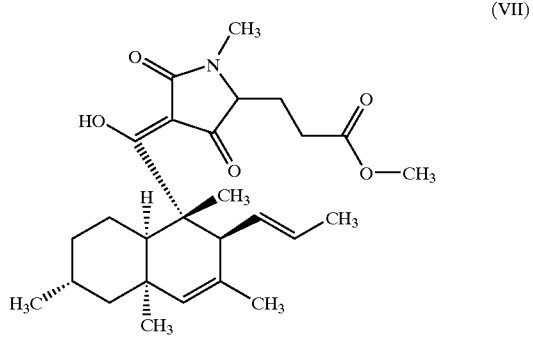

(VII)

or to a stereoisomeric form or a tautomeric form of a compound of the formula (IV), (V), (VI) or (VII) or to a mixture of the respective previously mentioned forms in any ratio, or to a physiologically tolerated salt of a compound of the formula (IV), (V), (VI) or (VII) or of a stereoisomeric form or of a tautomeric form of a compound of the formula (IV), (V), (VI) or (VII).

The inventive compounds differs from substances which are known from the literature, for example in their polarity, their chemical structure or their antimicrobial activity or other physical properties. In particular, as compared with the compounds in the prior art, the compounds according to the invention contain an additional methyl group in the naphthyl moiety.

The invention furthermore relates to obvious chemical equivalents of the compounds of the formulae (I) to (VI).

Obvious chemical equivalents of the compounds according to the invention are compounds which possess the same activity as the compounds according to the invention and exhibit a trivial chemical difference or which are converted, under mild conditions, into the compounds according to the invention. Said equivalents include, for example, esters, azomethines (Schiff's bases), ketals, oximes, hydrogenation products, reduction products, complexes or addition compounds of or with the compounds according to the invention.

For example, an activated acid, for example acid chlorides or other acid derivatives, can be reacted with the hydroxyl group of the compound of the formula (I), or of one or more double bonds and/or carbonyl groups of the compound of the formula (I) can be reduced with a reducing agent, with double bonds being reduced, for example, using $H_2$/Pd and carbonyl groups being reduced, for example, using $NaBH_4$. The abovementioned methods for derivatizing are described in text books such as Jerry March, Advanced Organic Chemistry, John Wiley & Sons, $4^{th}$ Edition, 1992. In order to carry out reactions selectively, it can be advantageous to introduce suitable protecting groups, in a manner known per se, prior to the reaction. The protecting groups are eliminated after the reaction and the reaction product is subsequently purified.

The invention furthermore relates to gabusectin, a compound which has the empirical formula $C_{25}H_{35}NO_4$, as demonstrated by ESI and FAB mass spectroscopy, and which is characterized by the $^1H$ NMR and $^{13}C$ NMR data given in table 2, or to a stereoisomeric form or a tautomeric form of the compound gabusectin, or to a mixture of the respective previously mentioned forms in any ratio, or to a physiologically tolerated salt of the compound gabusectin or of a stereoisomeric form or of a tautomeric form of the compound gabusectin.

The invention furthermore relates to gabusectin methyl ester, a compound of the empirical formula $C_{27}H_{39}NO_5$, demonstrated by ESI and FAB mass spectroscopy, and characterized by the $^1H$ NMR and $^{13}C$ NMR data given in table 3, or to a stereoisomeric form or a tautomeric form of the compound gabusectin methyl ester, or to a mixture of the respective previously mentioned forms in any ratio, or to a physiologically tolerated salt of the compound gabusectin methyl ester or of a stereoisomeric form or a tautomeric form of the compound gabusectin methyl ester.

The invention furthermore relates to a compound of the formula (I) which can be obtained by fermenting ST 003236 (DSM 14476), or a variant and/or mutants of ST 003236 (DSM 14476), in a culture medium until the compound of the formula (I) accumulates in the culture broth, then isolating the compound of the formula (I) and, where appropriate, converting it into a pharmacologically tolerated salt.

The invention also relates to a compound of the empirical formula $C_{26}H_{37}NO_5$ (Gabusectin) which can be obtained by fermenting ST 003236 (DSM 14476), or a variant and/or mutant of ST 003236 (DSM 14476) in a culture medium until the compound gabusectin accumulates in the culture broth, subsequently isolating the compound Gabusectin and, where appropriate, converting it into a pharmacologically tolerated salt.

The invention additionally relates to a process for preparing a compound of the formula (I), which comprises culturing the microorganism ST 003236 (DSM 14476), or a variant and/or mutant of ST 003236 (DSM 14476), in an aqueous nutrient medium, isolating and purifying a compound of the formula (I) and, where appropriate, converting it into an obvious chemical equivalent or a pharmacologically tolerated salt.

The invention furthermore relates to a process for preparing a compound of the formula (I), which comprises esterifying gabusectin of the formula (IV) with a $C_1$–$C_6$-alkyl-, $C_2$–$C_6$-alkenyl- or $C_2$–$C_6$-alkynyl-alcohol derivative, or with a $C_1$–$C_6$-alkyl-, $C_2$–$C_6$-alkenyl- or $C_2$–$C_6$-alkynyl-alkylating agent, to give a compound of the formula (I), in which alkyl, alkenyl and alkynyl are straight-chain or branched and can optionally be substituted, once or twice, by the radicals 2.1 to 2.9 in accordance with formula (I) in claim 1, in which the substituents 2.3 to 2.7 can be further substituted by —CN, -amide or -oxime functions, and $R_2$ is H, $R_3$ is $CH_3$, $R_4$ is —CH=CH—$CH_3$, $R_5$ is $CH_3$, and X, $X_2$, $X_3$, $X_4$ and $X_5$ are 0, preferably using a $C_1$–$C_6$-alkyl-alkylating agent, particularly preferably using a $C_1$-alkylating agent.

$C_1$–$C_6$-Alkyl-, $C_2$–$C_6$-alkenyl- or $C_2$–$C_6$-alkynyl-alcohol derivatives are straight-chain or branched and optionally substituted once or twice by the radicals 2.1 to 2.9, see above, in which the substituents 2.3 to 2.7 can be further substituted by —CN, -amide or -oxime functions, for example methanol, ethanol, n-propanol, isopropanol, n-butanol, sec-butanol, tert-butanol and n-hexanol, 2-buten-1-ol (crotyl alcohol), 1-propen-3-ol (allyl alcohol), 1,3-pentadien-5-ol, 1,4-pentadien-3-ol and 2-penten-1-ol, 1-penten-4-ol (allylmethylcarbinol), 1-penten-3-ol (ethylvinylcarbinol), 2-propyn-1-ol (propargyl alcohol), 1-butyn-3-ol, 2-butyn-1-ol, 3-butyn-1-ol, 1-pentyn-3-ol, 2-pentyn-1-ol, 3-pentyn-1-ol and 4-pentyin-1-ol, preferably methanol.

$C_1$–$C_6$-Alkyl-, $C_2$–$C_6$-alkenyl- or $C_2$–$C_6$-alkynyl-alkylating agents are straight-chain or branched and optionally substituted once or twice by the radicals 2.1 to 2.9, see above, for example diazomethane derivatives as $C_1$-alkylating agents, for example trimethylsilyldiazomethane.

Methods for esterifying are described, for example, in Jerry March, Advanced Organic Chemistry, John Wiley & Sons, 4th Edition, 1992.

The strain ST 003236 has been deposited in the Deutsche Sammiung von Microorganismen und Zelikulturen [German collection of microorganisms and cell cultures] GmbH (DSM), MascheroderWeg 1B, 38124 Braunschweig, Germany, in accordance with the rules of the Budapest Treaty, under the following number DSM 14476.

Said process comprises culturing ST 003236 (DSM 14476), its mutants or variants, under aerobic conditions in a culture media containing one or more carbon and nitrogen sources, inorganic salts and, where appropriate, trace elements.

The course of the fermentation, and the formation of the antibiotics according to the invention, can be monitored using methods known to a skilled person, for example by testing the biological activity in bioassays or by means of chromatographic methods such as thin layer chromatography (TLC) or high performance liquid chromatography (HPLC).

A mutant is a microorganism in which one or more genes in the genome has/have been modified, with the gene or genes which is/are responsible for the ability of the organism to produce the compound according to the invention remaining functional and inheritable.

Such mutants can be generated, in a manner known per se, by physical means, for example irradiation, such as with ultraviolet rays or X-rays, or using chemical mutagens, such as ethyl methanesulfonate (EMS); 2-hydroxy-4-methoxy-benzo-phenone (MOB) or N-methyl-N'-nitro-N-nitrosoguanidine (MNNG), or as described by Brock et al. in "Biology of Microorganisms", Prentice Hall, pages 238-247 (1984).

A variant is a phenotype of the microorganism. Microorganisms have the ability to adapt to their environment and therefore demonstrate pronounced physiological flexibility. In phenotypic adaptation, all the cells in the microorganism are involved, with the nature of the change not being genetically conditioned and being reversible under altered circumstances (H. Stolp, Microbial ecology: organism, habitats, activities. Cambridge University Press, Cambridge, GB, page 180, 1988).

Screening for mutants and variants which produce the antibiotic according to the invention can be carried out by determining the biological activity of the active compound which has accumulated in the culture broth, for example by determining its antibacterial effect, or by detecting compounds, which are known to be antibacterially active, in the fermentation broth using HPLC or LC-MS methods, for example.

The compound gabusectin is found both in the mycelium and in the culture filtrate. It is therefore expedient to separate the fermentation solution into the culture filtrate and the mycelium by means of filtration and to dry these fractions separately. The dried culture filtrate and the dried mycelium are expediently extracted separately with an organic solvent, for example methanol or 2-propanol.

While the extraction can be carried out over a wide pH range, it is expedient to carry it out in a neutral or weakly acidic medium, preferably between pH 3 and pH 7. The extract can, for example, be concentrated and dried in vacuo.

One method of isolating the antibiotic according to the invention [lacuna] in accordance with the polarity separation principle, in a manner known per se.

Another method of purification is chromatography on adsorption resins, for example on Diaion® HP-20 (Mitsubishi Casei Corp., Tokyo), on Amberlite® XAD 7 (Rohm and Haas, USA), on Amberchrom® CG, (Toso Haas, Philadelphia, USA) or on similar materials. A large number of reverse-phase supports, such as $RP_8$ and $RP_{18}$, as have become well known, for example, within the context of high pressure liquid chromatography (HPLC), are also suitable.

Another possibility for purifying the compound according to the invention is that of using what are termed normal-phase chromatography supports, such as silica gel or $A_6O_3$, or other supports, in a manner known per se.

An alternative isolation method is that of using molecular sieves, such as Fractogelo TSK HW-40 (Merck, Germany) and others, in a manner known per se. In addition to this, it is also possible to isolate the gabusectin by crystallization from enriched material. Organic solvents and their mixtures, either anhydrous or containing added water, are, for example, suitable for this purpose. An additional method for isolating and purifying the antibiotics according to the invention is that of using anion exchangers, preferably in a pH range of from 4 to 10, and cation exchangers, preferably in a pH range of from 2 to 5. The use of buffer solutions to which quantities of organic solvents have been added is particularly suitable for this purpose. Gabusectin, the said chemical derivatives thereof, and the obvious chemical equivalents thereof, can be converted into the corresponding pharmacologically tolerated salts using methods known to a skilled person.

Pharmacologically tolerated salts of the compounds according to the invention are understood as being both inorganic and organic salts, as are described in Remington's Pharmaceutical Sciences (17th edition, page 1418 [1985]). Suitable salts are, in particular, alkali metal salts, ammonium salts, alkaline earth metal salts, salts with physiologically tolerated amines and salts with inorganic or organic acids, such as HCl, HBr, $H_2SO_4$, maleic acid, and fumaric acid.

It has been found, surprisingly, that the compounds of the formula (I) according to the invention exhibit antibacterial effects and are therefore suitable for the treatment of diseases which are caused by bacterial infection. Table 1 summarizes the minimum inhibitory concentrations (MICs) of gabusectin, by way of example.

TABLE 1

In-vitro antibacterial activity of the compound gabusectin in a serial dilution test.

| Bacterium (strain) | MIC values ($\mu$g/ml) |
| --- | --- |
| S. aureus (SG511) | 5 |
| S. aureus (Exp54146) | 20 |
| S. pyogenes (A561) | 20 |
| E. faecium (M78L) | 40 |

Gabusectin is well-tolerated at and above its effective concentration.

The present invention therefore also relates to the use of one or more of the compounds of the formula (I) to (VII) according to the invention as pharmaceuticals, and the use of one or more of the compounds of the formula (I) to (VI) according to the invention for producing pharmaceuticals, in particular for the treatment and/or prophylaxis of bacterial infections.

The present invention furthermore relates to a pharmaceutical which has a content of one or more compounds according to the invention.

Said pharmaceutical comprising a compound of the formula (I) is produced using one or more physiological auxiliary substances and brought into a suitable administration form.

The pharmaceuticals according to the invention can be used enterally (orally), parenterally (intramuscularly or intravenously), rectally or locally (topically). They can be administered in the form of solutions, powders (tablets and capsules, including microcapsules), ointments (creams or gels), or suppositories. Suitable auxiliary substances for such formulations are the pharmaceutically customary liquid or solid fillers and extenders, solvents, emulsifiers, glidants, taste corrigents, dyes and/or buffering substances. 0.1-1000, preferably 0.2-100, mg/kg of body weight is/are administered as an expedient dose. The doses are expediently administered in dosage units which contain at least the effective daily quantity of the compounds according to the invention, for example 30-3000, preferably 50-1000, mg.

The following examples are intended to be used for clarifying the invention without in any way restricting its scope.

EXAMPLE 1

Preparing a Glycerol Culture of ST 003236 (DSM 14476).

30 ml of nutrient solution (malt extract, 2.0%, yeast extract, 0.2%, glucose, 1.0%, $(NH_4)_2HPO_4$, 0.05%, pH 6.0) were inoculated with the strain ST 003236 (DSM 14476) in a sterile 100 ml Erlenmeyer flask and incubated for 6 days, at 25° C. and 140 rpm, on a rotating shaker. 1.5 ml of this culture were then diluted with 2.5 ml of 80% glycerol and stored at −135° C.

EXAMPLE 2

Preparing a Preliminary Culture of ST 003236 (DSM 14476) in an Erlenmeyer Flask.

100 ml of nutrient solution (malt extract, 2.0%, yeast extract, 0.2%, glucose, 1.0%, $(NH_4)_2HPO_4$, 0.05%, pH 6.0) were inoculated with an ampoule of the strain ST 003236 (DSM 14476) in a sterile 300 ml Erlenmeyer flask and incubated for 6 days at 25° C. and 140 rpm. 2 ml of this preliminary culture were subsequently inoculated for preparing the main cultures.

EXAMPLE 3

Preparing a Liquid Main Culture of ST 003236 (DSM 14476).

A sterile 300 ml Erlenmeyer flask containing 100 ml of the following nutrient solution: potato dextrose, 2.4%, yeast extract, 0.2%, was inoculated with a culture grown on a sloping tube (same nutrient solution but containing 2% agar) or with 2 ml of a preliminary culture (see example 2) and incubated, at 140 rpm and 25° C., on a shaker. The maximum production of one or more compounds of the formula (I) according to the invention was reached after approx. 144 hours. A 96 hour-old submerged culture from the same nutrient solution (inoculation quantity, approx. 10%) was adequate for inoculating fermenters of from 10 to 200 I in volume. The conditions for these fermenters were:
Temperature: 25° C.
Stirrer speed: 200 rpm
Aeration: 15 I. Min⁻.

It was possible to suppress foam formation by repeatedly adding ethanolic polyol solution. The production maximum was achieved after approx. 96 to 144 hours.

EXAMPLE 4

Isolating the Compound Gabusectin.

3I of culture solution, obtained as described in example 3, were filtered and the culture filtrate and the mycelium were freeze-dried separately. The dried culture filtrate was extracted with 3 liters of methanol. The clear liquid phase was concentrated down to 200 ml in vacuo and filtered. This methanol solution was mixed with water in a ratio of 9:1 in an HPLC high pressure gradient unit and loaded onto a 300 ml-capacity column filled with the adsorption resin MCI Gel® CHP20P (Mitsubishi Casei Corp., Tokyo). Column dimensions: width×height: 5 cm×15 cm. The column was eluted with a solvent gradient of water to 100% methanol and the outflow from the column (50 ml/minute) was collected in fractions of in each case 25 ml in volume. The gabusectin-containing fractions 65 to 75, which were checked by HPLC analyses, were collected and concentrated in vacuo and freeze-dried (0.23 g).

EXAMPLE 5

Purifying Gabusectin by High Pressure Liquid Chromatography (HPLC).

| | |
|---|---|
| Column: | Purospher® STAR RP-18 e 3 µm, 30-2, (Merck, Germany) |
| Mobile phase buffer A: | 5% acetonitrile + 0.1% ammonium acetate, |
| Mobile phase buffer B: | 95% acetonitrile + 0.1% ammonium acetate, |
| Gradient: | 15 min |
| Flow rate: | 0.25 ml per minute |

Detection by UV absorption at 210 nm.

Gabusectin was found to have a retention time of 6.5 min.

EXAMPLE 6

Final Purification of Gabusectin.

The enriched antibiotic gabusectin (0.23 g), obtained as described in example 4, was fractionated on a LUNAR 10 µm C 18(2) HPLC column (Phenomenex, USA) (width× height=2.1 cm×25 cm) by the gradient method using from 5% to 95% acetonitrile in 0.05% trifluoroacetic acid. Flow rate: 25 ml/min. Fraction size: 25 ml. Fraction 48, which was examined by analytical HPLC (see example 5) was freeze-dried. It yielded 50 mg of gabusectin at 98% purity.

EXAMPLE 7

Characterizing Gabusectin.

The physicochemical and spectroscopic properties of the antibiotic according to the invention can be summarized as follows:
Appearance:
Colorless to pale yellow substance which is soluble in medium-polar and polar organic solvents but not particularly soluble in water. Stable in neutral and mildly acidic medium but unstable in strongly acidic and strongly alkali solution.

| | |
|---|---|
| Empirical formula: | $C_{26}H_{37}NO_5$ |
| Molecular weight: | 443.59 |
| $^1$H NMR and $^{13}$C NMR: | see table 2 |
| UV maxima: | 236 nm and 294 nm |

Determining the Molar Peak:
The mass of 443 is assigned to the sought-after molecule on the basis of the following findings: ESI+spectrum and FAB⁺ spectra exhibit peaks at 444 amu (M+H)⁺. ESI spectrum exhibits a peak at 442 amu (M−H). High resolution of the quasi molecule ion: FAB+ 444.27424 (M+H)+. 443.59 was calculated for the empirical formula C$_{26}$H$_{37}$NO$_5$.

TABLE 2

$^1$H- and $^{13}$C-chemical shifts of gabusectin in CDCl$_3$ at 275 K.

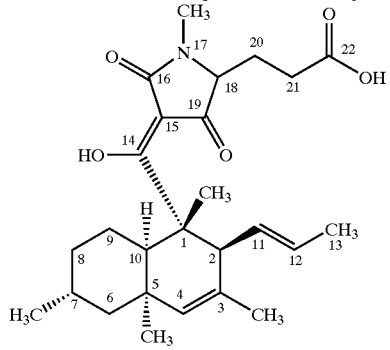

| Position | $^{13}$C δ (ppm) | $^1$H δ (ppm) | HMBC correlations ($^{13}$C- $^1$H) |
|---|---|---|---|
| 1 | 49.01 | — | H3-Me(w), H1-Me, H2(w), H10, 14-OH |
| 1-Me | 20.77 | 1.24 s | — |
| 2 | 45.69 | 3.36 | H3-Me, H9', H1-Me, H10, H4, H12(s), H11(w) |
| 3 | 132.86 | — | H11(w), H2, H3-Me(s), H6'(w) |
| 3-Me | 23.43 | 1.69 s | H4 |
| 4 | 130.04 | 5.06 | H2, H10, H3-Me(s), H6', H5-Me(s) |
| 5 | 37.61 | — | H6', H7-Me(w), H5-Me(s), H10, H4(s) |
| 5-Me | 31.91 | 0.70 | H3-Me, H6', H10(w) |
| 6 | 51.62 | 1.36, 0.92 | H3-Me(w), H9', H7-Me, H5-Me, H4(w) |
| 7 | 29.46 | 1.26 | H6(w), H6', H9(w), H7-Me(s), H5-Me(w) |
| 7-Me | 22.41 | 0.81 d | — |
| 8 | 34.97 | 1.65, 0.87 | H9(w), H9'(w), H6(w), H6', H7-Me(s) |
| 9 | 25.52 | 1.84, 1.29 | H10 |
| 10 | 42.17 | 2.66 dd | H9', H1-Me, H5-Me, H2(w), H4 |
| 11 | 132.25 | 5.31 | H12, H2(w), H13(s) |
| 12 | 128.95 | 5.44 | H11, H2, H13(s) |
| 13 | 17.90 | 1.69 | H12, H11 |
| 14 | 203.37 | — | 14-OH, H2, H10, H1-Me |
| 14-OH | — | 17.73 | — |
| 15 | 98.81 | — | 14-OH |
| 16 | 177.05 | — | 14-OH, H18(s), H17-Me(s) |
| 17-Me | 27.20 | 3.02 s | — |
| 18 | 64.27 | 3.76 dd | H17-Me, H20, H20' |
| 19 | 190.36 | — | H18, H20(w), H20' |
| 20 | 23.27 | 2.32, 2.08 | H21, H18 |
| 21 | 27.44 | 2.30, 2.30 | H20, H20', H18 |
| 22 | 178.18 | — | H20, H21 |
| 22-COOH | — | 7.1 br | — |

EXAMPLE 8

Inhibitory effect of Gabusectin in the Agar Diffusion Test

Agar plates containing 2 ml of *Staphylococcus aureus* inoculum in 200 ml of agar solution were prepared. gabusectin was applied, in a 10 mM solution, to 6 mm-diameter paper disks, which were then laid on the agar plate. The inoculated *Staphylococcus* plates were incubated at 37° C. for 16 hours. Inhibition halos having the following diameters (mm) were then observed:

| Quantity | Inhibition halo size (mm) |
|---|---|
| 10 μL | 8 |
| 20 μL | 14 |
| 40 μL | 17 |

EXAMPLE 9

Methylation, and Subsequent Purification of the Gabusectin Methyl Ester.

20 mg of the antibiotic gabusectin (0.045 mmol), obtained as described in example 6, were dissolved in 5 ml of MeOH, after which trimethylsilyldiazomethane was added in a 6-fold molar excess. The reaction mixture was left to stand at room temperature for 60 min and then concentrated to dryness. The resulting mixture was fractionated chromatographically on a LUNA® 5 μm C 18(2) HPLC column (Phenomenex, USA) (width×height=1 cm×25 cm) by the gradient method using from 5% to 95% acetonitrile in 0.05% trifluoroacetic acid. Flow rate: 6.5 ml/min. Fraction size: 6.5 ml. Fraction 61, which was examined by analytical HPLC (see example 5), was freeze-dried. It yielded 7.4 mg of gabusectin methyl ester at 97% purity.

EXAMPLE 10

Characterizing Gabusectin Methyl Ester.

The physicochemical and spectroscopic properties of the antibiotic according to the invention can be summarized as follows:

Appearance:

Colorless to pale-yellow substance which is soluble in medium-polar and polar organic solvents but not particularly soluble in water. Stable in neutral and mildly acidic medium but unstable in strongly acidic and strongly alkaline solution.

| | |
|---|---|
| Empirical formula: | C$_{27}$H$_{39}$NO$_5$ |
| Molecular weight: | 457.62 |
| $^1$H NMR and $^{13}$C NMR: | see table 3 |
| UV maxima: | 236 nm and 294 nm |

Determination of the Molar Peak:

The mass of 457.6 is assigned to the sought-after molecule on the basis of the following findings: ESI+ spectrum and FAB+ spectra exhibit peaks at 457 amu (M+H)+. ESI− spectra exhibits a peak at 458.5 amu (M−H)−.

TABLE 3

¹H and ¹³C chemical shifts of gabusectin methyl ester in CDCl₃ at 275 K.

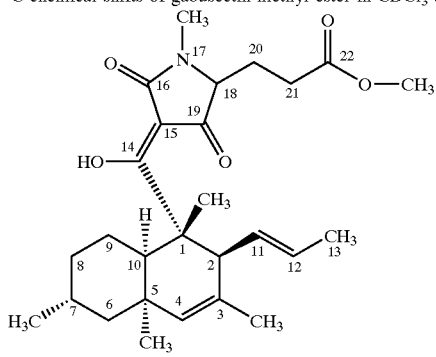

| Position | ¹³C δ (ppm) | ¹H δ (ppm) | HMBC correlations (¹³C- ¹H) |
|---|---|---|---|
| 1 | 48.89 | — | H3-Me(w), H1-Me, H10(w) |
| 1-Me | 20.83 | 1.24 | — |
| 2 | 45.70 | 3.36 | H3-Me, H1-Me, H9', H10(w), H12, H4 |
| 3 | 132.86 | — | H3-Me |
| 3-Me | 23.44 | 1.68 | H4 |
| 4 | 130.08 | 5.05 | H3-Me, H6', H5-Me, H10(w) |
| 5 | 37.63 | — | H6', H5-Me, H10(w), H4(w) |
| 5-Me | 31.91 | 0.70 | H10(w), H6', H3-Me(w) |
| 6 | 51.65 | 1.35, 0.92 | H9', H7-Me, H5-Me, H4(w) |
| 7 | 29.48 | 1.25 | H6', H7-Me |
| 7-Me | 22.42 | 0.80 | — |
| 8 | 35.00 | 1.64, 0.88 | H6', H7-Me(s) |
| 9 | 25.55 | 1.83, 1.30 | H10 |
| 10 | 42.17 | 2.67 | H1-Me, H5-Me, H9', H4(w) |
| 11 | 132.35 | 5.30 | H12, H13 |
| 12 | 128.87 | 5.43 | H11, H13 |
| 13 | 17.90 | 1.69 | H12, H11 |
| 14 | 202.86 | — | H1-Me |
| 14-OH | — | 17.75 | — |
| 15 | 98.91 | — | — |
| 16 | 177.06 | — | H17-Me |
| 17-Me | 27.13 | 3.02 | — |
| 18 | 64.49 | 3.71 | H20, H20', H21, H17-Me |
| 19 | 190.33 | — | H18, H20' |
| 20 | 23.52 | 2.29, 2.11 | H21 |
| 21 | 27.42 | 2.23, 2.23 | — |
| 22 | 173.05 | — | 22-OMe, H20, H20', H21 |
| 22-OMe | 51.93 | 3.66 | — |

EXAMPLE 11

Inhibitory Effect of the Gabusectin Methyl Ester in the Agar Diffusion Test.

Agar plates containing 2 ml of *Staphylococcus aureus* inoculum in 200 ml of agar solution were prepared. gabusectin methyl ester is applied, in a 10 mM solution, to 6 mm-diameter paper disks, which are then laid on the agar plate. The inoculated *Staphylococcus* plates were incubated at 37° C. for 16 hours. Inhibition halos having the following diameters (mm) were then observed.

| Quantity | Inhibition halo size (mm) |
|---|---|
| 10 μL | 0 |
| 20 μL | 7 |
| 40 μL | 8 |

What is claimed is:

1. A compound of formula (I)

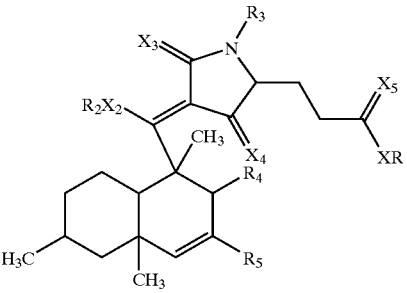

(I)

wherein

R, $R_2$ and $R_3$ are each, independently,

H, or $C_1$–$C_6$-alkyl, $C_2$–$C_6$-alkenyl or $C_2$–$C_6$-alkynyl, wherein the alkyl, alkenyl and alkynyl are straight-chain or branched and are optionally substituted, once or twice, by:

—OH,

=O,

—O—$C_1$–$C_6$-alkyl, wherein the alkyl is straight-chain or branched,

—O—$C_2$–$C_6$-alkenyl, wherein the alkenyl is straight-chain or branched,

—aryl,

—NH—$C_1$–$C_6$-alkyl, wherein the alkyl is straight-chain or branched,

—NH—$C_2$–$C_6$-alkenyl, wherein the alkenyl is straight-chain or branched,

—$NH_2$ or halogen, wherein the alkyl, alkenyl and aryl portions of —O—$C_1$–$C_6$-alkyl, —O—$C_2$–$C_6$-alkenyl, -aryl, —NH—$C_1$–$C_6$-alkyl, and —NH—$C_2$–$C_6$-alkenyl can be further substituted by —CN, -amide or -oxime;

R4 is $C_1$–$C_6$-alkyl or $C_2$–$C_6$-alkenyl, wherein the alkyl and alkenyl can be straight-chain or branched and are optionally substituted once or twice by:

—OH,

=O,

—O—$C_1$–$C_6$-alkyl, wherein the alkyl is straight-chain or branched,

—O—$C_2$–$C_6$-alkenyl, wherein the alkenyl is straight-chain or branched,

-aryl,

—NH—$C_1$–$C_6$-alkyl, wherein the alkyl is straight-chain or branched,

—NH—$C_2$–$C_6$-alkenyl, wherein the alkenyl is straight-chain or branched,

—$NH_2$ or halogen, wherein the alkyl, alkenyl and aryl portions of —O—$C_1$–$C_6$-alkyl, —O—$C_2$–$C_6$-alkenyl, -aryl, —NH—$C_1$–$C_6$-alkyl, and —NH—$C_2$–$C_6$-alkenyl can be further substituted by —CN, -amide or -oxime;

$R_5$ is H or methyl; and

X, $X_2$, $X_3$, $X_4$ and $X_5$, are each independently O, NH, N—$C_1$–$C_6$-alkyl, N—$C_2$–$C_6$-alkenyl, N—$C_2$–$C_6$-alkynyl, N-acyl, N-aryl, N—O—R or S, or a stereoisomeric form or a tautomeric form of the compound of formula (I), or a physiologically tolerated salt of the compound of formula (I) or of a stereoisomeric form or of a tautomeric form of the compound of formula (I).

2. The compound according to claim 1, wherein

R is H, or

C$_1$–C$_6$-alkyl, C$_2$–C$_6$-alkenyl or C$_2$–C$_6$-alkyntyl, wherein the C$_1$–C$_6$-alkyl, C$_2$–C$_6$-alkenyl and C$_2$–C$_6$-alkynyl are straight-chain or branched and are optionally substituted once or twice by:

=O,

=O-C$_1$–C$_6$-alkyl, wherein the alkyl is straight-chain or branched,

=O—C$_2$–C$_6$alkenyl, wherein the alkenyl is straight-chain or branched,

-aryl,

—NH—C$_1$–C$_6$-alkyl, wherein the alkyl is straight-chain or branched,

—NH—C$_2$–C$_6$-alkenyl, wherein the alkenyl is straight-chain or branched,

—NH$_2$ or halogen, wherein the alkyl, alkenyl and aryl portions of —O—C$_1$–C$_6$-alkyl, —O—C$_2$–C$_6$-alkenyl, -aryl, —NH—C$_1$–C$_6$alkyl, and —NH—C$_2$–C6-alkenyl can be further substituted by —CN, -amide or -oxime;

R$_2$ is H,

R$_3$ is CH$_3$,

R4 is —CH=CH—CH$_3$

R$_5$ is CH$_3$, and

X, X$_2$, X$_3$, X$_4$ and X$_5$ are O.

3. The compound according to claim 1, wherein

R is H,

R$_2$ is H or CH$_3$,

R$_3$ is CH$_3$,

R4 is —CH=CH$_3$,

R$_5$ is CH$_3$, and

X, X$_2$, X$_3$, X$_4$ and X$_5$ are O.

4. The compound according to claim 1 of formula (IV)

(IV)

or a stereoisomeric form or a tautomeric form of a compound of formula (IV), or a physiologically tolerated salt of the compound of formula (IV) or of a stereoisomeric form or of a tautomeric form of the compound of formula (I).

5. The compound according to claim 1 of formula (V)

(V)

or a stereoisomeric form or a tautomeric form of a compound of formula (V), or a physiologically tolerated salt of a the compound of formula (V) or of a stereoisomeric form or of a tautomeric form of the compound of formula (V).

6. The compound according to claim 1 of formula (VI)

(VI)

or a stereoisomeric form or a tautomeric form of a compound of formula (VI), or a physiologically tolerated salt of the compound of formula (VI) or of a stereoisomeric form or of a tautomeric form of the compound of formula (VI).

7. The compound according to claim 1 of formula (VII)

(VII)

or a stereoisomeric form or a tautomeric form of a compound of formula (VII) or a physiologically tolerated salt of the compound of formula (VII) or of a stereoisomeric form or of a tautomeric form of the compound of formula (VII).

8. A process for preparing a compound of formula (I) as claimed in claim 1, which comprises culturing the microorganism ST 003236 (DSM 14476), or a variant and/or mutant of ST 003236 in an aqueous nutrient medium, isolating and purifying the compound of formula (1), and, where desired, converting it into an obvious chemical equivalent or a pharmacologically tolerated salt.

9. The process as claimed in claim 8, wherein the microorganism ST 003236 (DSM 14476) or a mutant and/or variant of ST 003236 is fermented, under aerobic conditions, in a culture medium containing one or more carbon and nitrogen sources, and inorganic salts, and optionally, trace elements.

10. The process as claimed in claim 8 or 9, wherein the fermentation under aerobic conditions is carried out at a temperature between 20 and 35° C. and at a pH of between 4 and 10.

11. A process for preparing a compound of formula (I) as claimed in claim 1, wherein R is $C_1$–$C_6$-alkyl-, $C_2$–$C_6$-alkenyl- or $C_2$–$C_6$-alkynyl, $R_2$ is H, $R_3$ is $CH_3$, $R_4$ is —CH=CH—$CO_3$, $R_5$ is $CH_3$, and X, $X_2$, $X_3$, $X_4$ and $X_5$ are O, that comprises esterifying a compound of formula (TV) as claimed in claim 4, with a $C_1$–$C_6$-alkyl-, $C_2$–$C_6$-alkenyl- or $C_2$–$C_6$-alkynyl-alcohol derivative or with a $C_1$–$C_6$-alkyl-, $C_2$–$C_6$-alkenyl- or $C_2$–$C_6$-alkynyl-alkylating agent to give the compound of formula (1), wherein the alkyl, alkenyl and alkynyl arc straight-chain or branched and can be optionally substituted once or twice by;

—OH,

=O,

—O—$C_1$–$C_6$-alkyl, wherein the alkyl is straight-chain or branched,

—O—$C_2$–$C_6$-alkenyl, wherein the alkenyl is straight-chain or branched,

-aryl

—NH-$C_1$–$C_6$-alkyl, wherein the alkyl is straight-chain or branched,

—NH—$C_2$–$C_6$-alkenyl, wherein the alkenyl is straight-chain or branched,

—$NH_2$ or halogen, wherein the alkyl, alkenyl and aryl portions of —O—$C_1$–$C_6$-alkyl, —O—$C_2$–$C_6$-alkenyl, -aryl, —NH—$C_1$–$C_6$-alkyl, and —NH—$C_2$–$C_6$-alkenyl can be further substituted by CN, -amide or -oxime.

12. The process for preparing the compound of formula (1) as claimed in claim 11, wherein the esterification is carried out using a $C_1$-alkylating agent.

13. A method for the treatment of an infectious disease caused by bacteria, in a patient in need thereof, comprising administering to the patient a pharmaceutically effective amount of a compound as claimed in any one of claims 1.

14. A pharmaceutical composition comprising at least one compound as claimed in claim 1 and one or more physiologically suitable auxiliary substances.

* * * * *